United States Patent [19]

McMorrow et al.

[11] Patent Number: 5,235,985
[45] Date of Patent: Aug. 17, 1993

[54] AUTOMATIC BLADDER SCANNING APPARATUS

[76] Inventors: Gerald J. McMorrow, 11810 N. E. 102nd Pl., Kirkland, Wash. 98033; William L. Barnard, 19622 65th Ave. NE., Seattle, Wash. 98155; Steven Bi, 14009 32nd Ave. NE. #202, Seattle, Wash. 98125

[21] Appl. No.: 877,448

[22] Filed: Apr. 30, 1992

[51] Int. Cl.$^5$ .............................................. A61B 8/00
[52] U.S. Cl. ........................... 128/660.07; 128/661.1; 128/916; 73/861.25
[58] Field of Search ...................... 128/660.07, 660.02, 128/661.02, 661.1, 916; 73/610, 861.25

[56] References Cited

U.S. PATENT DOCUMENTS

| | | | |
|---|---|---|---|
| 4,341,120 | 7/1982 | Anderson | 128/916 |
| 4,594,662 | 6/1986 | Devaney | 128/916 |
| 4,747,411 | 5/1988 | Ledley | 128/916 |
| 4,926,871 | 5/1990 | Ganguly et al. | 128/660.07 |
| 5,078,145 | 1/1992 | Furuhata | 128/916 |

Primary Examiner—Kyle L. Howell
Assistant Examiner—George Manuel
Attorney, Agent, or Firm—Clark A. Puntigam

[57] ABSTRACT

The automatic bladder scanning apparatus includes a transducer assembly (30), which includes a plurality of individual transducer elements (32). A first plurality of transducer elements are connected into an approximately circular or octagonal arrangement to produce a transmitted signal beam. The data transmission signal is pseudo-random. The returning echo signal is received by another plurality of transducer elements arranged in a preselected pattern. One receiving pattern includes two orthogonal sets of linear arrays, while the other receiving pattern involves an octagonal arrangement. The received signals from the second plurality of transducer elements are processed to form a composite received signal. The composite received signal is then further processed to produce information concerning the three dimension image of the bladder, which information is then used to calculate the bladder volume.

71 Claims, 8 Drawing Sheets

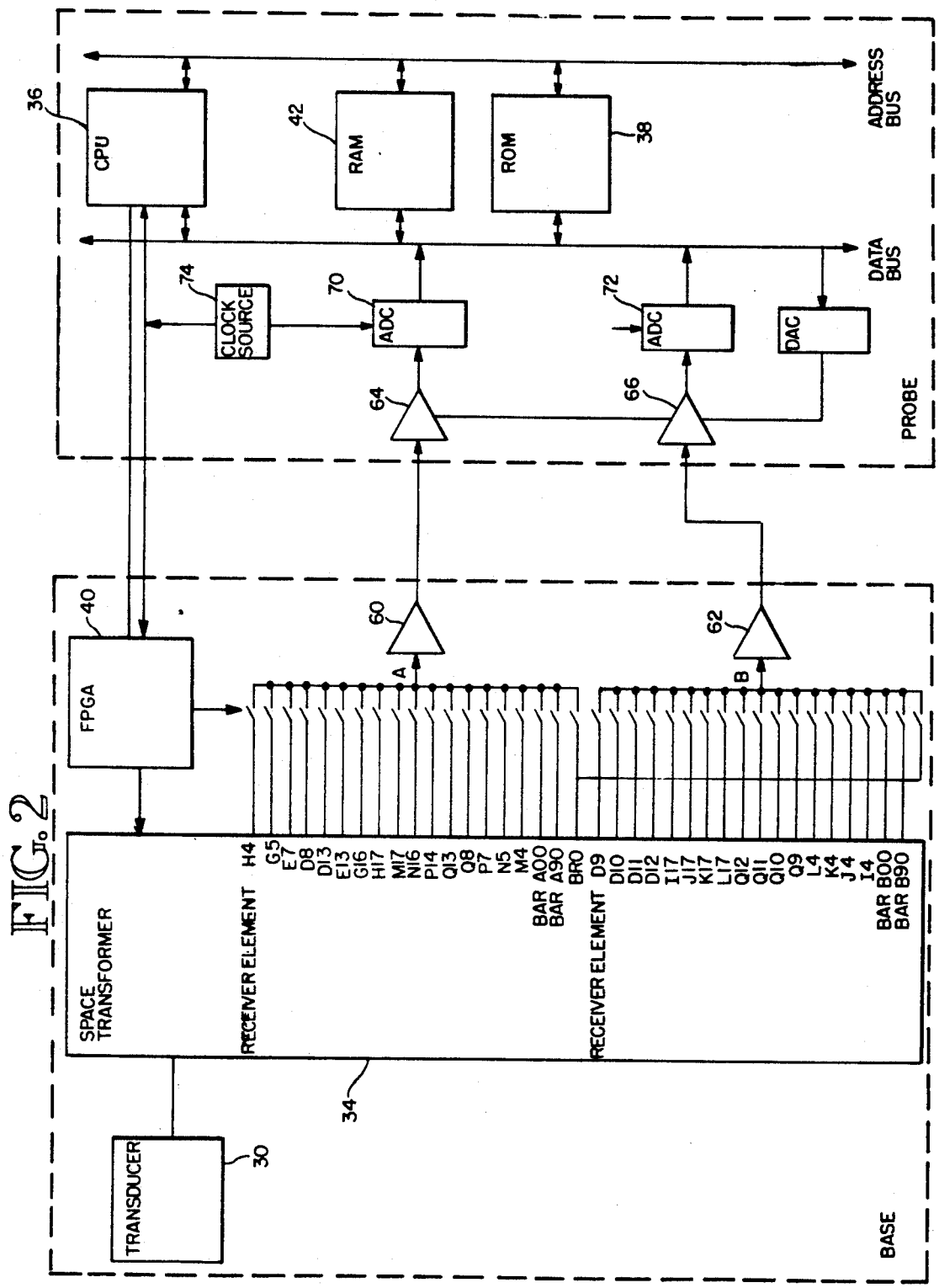

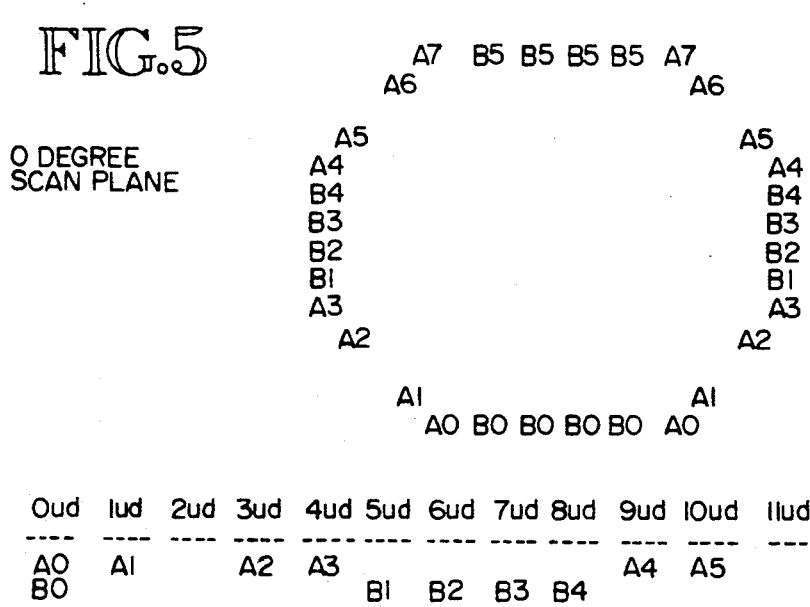
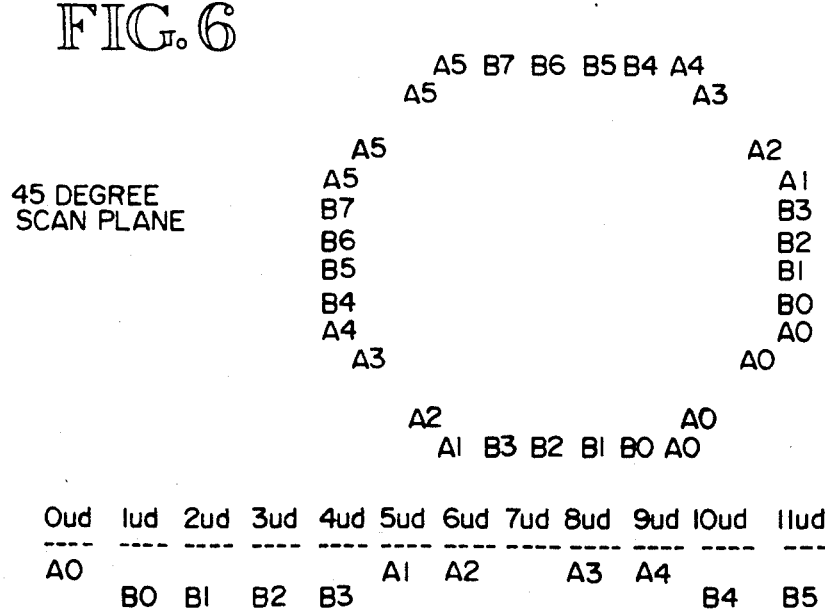

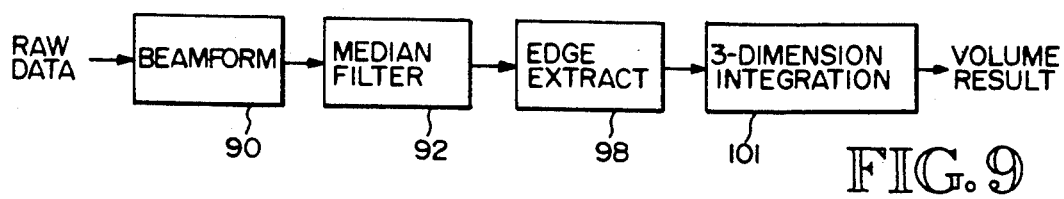
FIG. 9
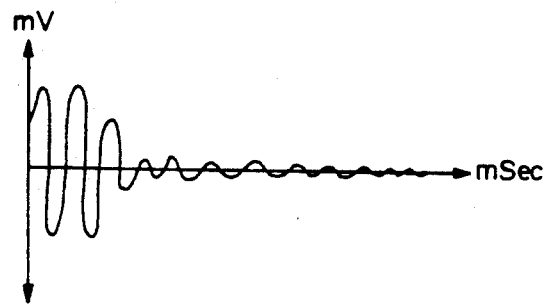
FIG. 10A
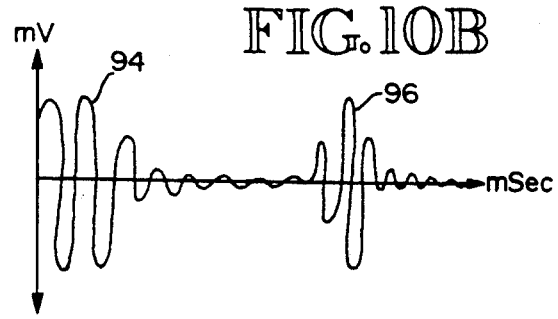
FIG. 10B
FIG. 12A
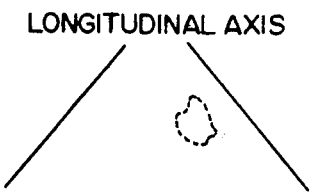
LONGITUDINAL AXIS
FIG. 12B
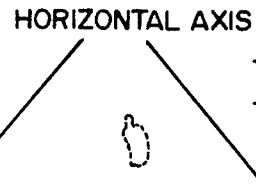
HORIZONTAL AXIS
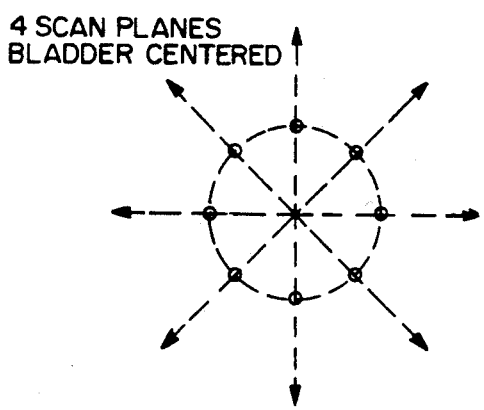
4 SCAN PLANES
BLADDER CENTERED
FIG. 13A
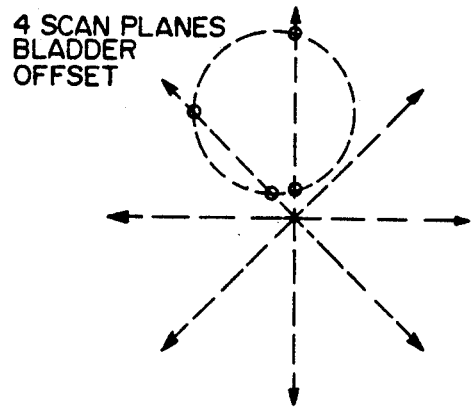
4 SCAN PLANES
BLADDER OFFSET
FIG. 13B

5,235,985

AUTOMATIC BLADDER SCANNING APPARATUS

TECHNICAL FIELD

This invention generally concerns an apparatus which automatically determines the volume of urine in the bladder and more specifically concerns an apparatus in which the bladder is completely and automatically imaged prior to the calculation of the volume of urine therein.

BACKGROUND OF THE INVENTION

An ultrasound apparatus for determining bladder volume is shown in U.S. Pat. No. 4,926,871, in the name of Dipankar Ganguly et al. That apparatus, involving an automatic calculation of bladder volume from ultrasound measurements of the major axis of the bladder and an axis perpendicular thereto, requires an operator to manipulate the scanhead transducer in a particular way to obtain the ultrasound measurements. An ellipsoid model is used as the basis for calculating bladder volume from the ultrasound measurements. The apparatus furthermore is used to determine bladder volume on an event-by-event basis and does not accumulate information from which long-term patterns or an accurate patient history could be developed. In addition to the above-mentioned apparatus, there are other sophisticated medical ultrasound machines which could be used to measure bladder volume, but these are typically limited to a single imaging plane (B-mode scanning) and require an operator to obtain the necessary ultrasound information. In addition, the bladder outline would have to be determined from that ultrasound information and then the volume calculations performed. Such a capability is not currently available on any medical ultrasound machine.

In addition to obtaining accurate bladder volume event information, it is desirable to have a bladder volume instrument which is completely automatic and which can be conveniently carried on the person of the user, so that historical information on bladder volume can be developed on a continuing basis.

DISCLOSURE OF THE INVENTION

Accordingly, the present invention includes a transmitter which comprises a plurality of transmitting transducer elements arranged in a preselected pattern, producing a transmitting beam which can be directed toward a bladder or other bodily organ; means for energizing the transmitting transducer elements to produce a transmitted signal comprising a series of complex signal bursts; means for receiving an echo signal from the bladder and producing information representative of the image of the bladder in three dimensions; and means for calculating the volume of the bladder or other organ.

Another aspect of the invention includes a transmitter for producing a transmitting beam which is directed toward the bladder; means for automatically controlling the transmitter so as to produce a plurality of spaced scan line signals within a first scan plane at a selected angle and within successive scan planes at successive selected angles; and means for receiving an echo signal from the bladder and producing information representative of the image of the bladder in three dimensions.

A further aspect of the invention includes a transmitter for producing a transmitting beam which is directed toward the bladder; means for receiving an echo signal from the bladder and producing information representative of the image of the bladder in three dimensions; means for calculating the volume of the bladder, and hence the amount of urine in the bladder, from said representative information; and means for storing the volume information over time, so as to provide a history of bladder volume information for a patient, wherein the apparatus is adapted so as to be carried on a patient during daily activity.

Still another aspect of the invention includes a transmitter which comprises a plurality of transmitter transducing elements arranged and connected in a pattern which defines an open center area in which there are no transmitter transducing elements, producing a transmitting signal beam which can be directed toward a bodily organ; means for receiving an echo signal from the organ; and means responsive to said echo signal to produce information representative of the image of at least a portion of the organ.

BRIEF DESCRIPTION OF THE DRAWINGS

FIG. 2 is an overall block diagram of the apparatus of the present invention.

FIGS. 5 and 6 are transmitting/receiving element patterns for one receiver embodiment.

FIG. 9 is a block diagram showing the sequence of steps in the calculation of bladder volume.

FIGS. 10A and 10B are signal diagrams showing a received scan line signal.

FIGS. 12A and 12B are diagrams for the outline of a bladder in two scan planes.

FIGS. 13A and 13B are diagrams showing frontal plane sections of a bladder for a plurality of scan planes, with the bladder being in different positions.

BEST MODE FOR CARRYING OUT THE INVENTION

Figure 4:
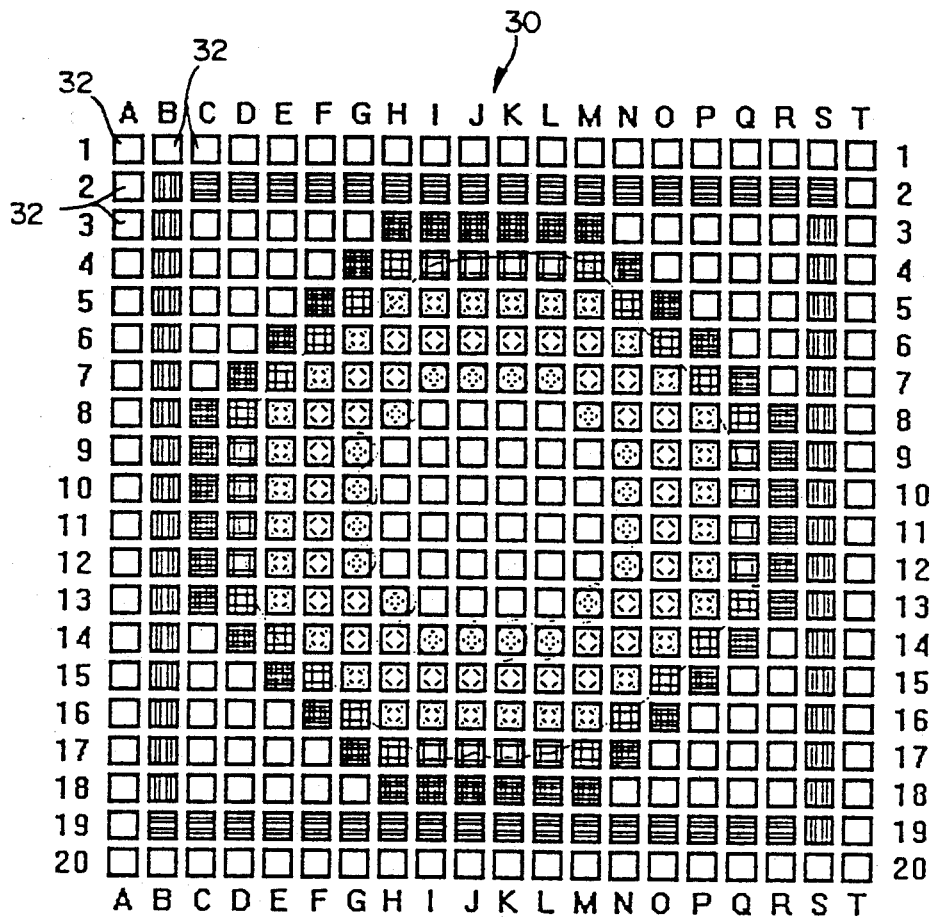
FIG. 4 is a diagram showing in detail the transducer portion of the present invention, including various transmitting and receiving configurations thereof.

Referring to FIG. 2, the apparatus of the present invention includes a transducer shown generally at 30, which comprises a matrix of individual transducer elements 32–32, shown in more detail in FIG. 4. In the embodiment shown, transducer 30 comprises 400 such individual elements, arranged in a square, 20 elements on a side, although this arrangement and the number of elements could be varied. The transducer elements 32–32 are controlled through a hard wire interface apparatus 34, referred to as a space transformer, which in turn is controlled by a microprocessor 36, which obtains preprogrammed instructions from ROM (read-only memory) 38. Located between microprocessor 36 and interface 34 is a Field Programmable Gate Array (FPGA) device 40 which is a conventional assembly comprising a combination of RAM memory and various solid-state interconnect devices which perform particular functions, such as inverters, etc.

In the embodiment shown, a carrier frequency of 1 mHz is used. The transducer 30 is one inch square and is approximately one-half wavelength thick. Accordingly, each individual transducing element 32-32 appears to be a point source of radiation. In detail, elements 32-32 in the embodiment shown are 46 mil square (three-quarter wavelength) by 60 mil thick and are made from lead metaniobate. The dimensions of the transducing elements may be varied.

A portion of transducer 30 is energized in a phased-array manner to form an ultrasound beam. A composite wave front is formed by combining the radiation from a selected number of individual point source transducing elements and then steered so as to form a cone of radiation, which in the embodiment shown has a 100° solid angle. This physical arrangement of transducer elements defines the transmitting antenna.

The transmitting antenna may have various configurations. Referring to FIG. 4, one basic transmitting antenna configuration in the embodiment shown, comprising 32 individual transducing elements, is in the form of a donut or modified circle. This arrangement is shown as transmit ring 8 (for eight wavelength diameter) in FIG. 4. This particular configuration images a particular depth into the body. Control over the depth of the imaging, referred to as "focusing" the transmitted beam, can be accomplished in a number of ways. Conventionally, beam focusing requires a complex of small electronically controlled adjustments to alter the beam and/or a plurality of different antennas. In the present invention, three different phased-array transmitting antenna configurations are defined by three concentric rings of transducer element combinations. In the particular arrangement shown in FIG. 4, three concentric transducer element rings include a first transmit ring 8 (8 wavelength diameter), a second transmit ring 10 (10 wavelength diameter) and a third transmit ring 12 (12 wavelength diameter). Any combination of these rings may be enabled, providing different depth image capability.

When it is necessary to image as deep into the body as possible, all three rings will be enabled at the same time to get the widest possible antenna scope, with greatest antenna gain. The closest or shallowest image depth is achieved by the 12-wavelength ring. This arrangement has been found to produce a transmitting antenna which can be dynamically focused at relatively small expense, without significant complexity. The ring or donut-shaped transducer element array has been discovered to be advantageous relative to a solid disk transducer, which is the typical configuration, because there are no center elements in the ring embodiment to destructively interfere with each other during transmission. It should be understood, however, that the donut or circular configuration may be modified to some extent in shape in the arrangement of the present invention.

The signal which is transmitted by the transmitting antenna in the present invention is different than the conventional medical ultrasound signal. The signal is pseudo-random, with a carrier frequency of 1 mHz, as opposed to a typical ultrasound sequence of signals comprising sets of short duration, large amplitude pulses. A complex, pseudo-random data pulse signal is produced from ROM and is applied to the transducer.

Figure 3:
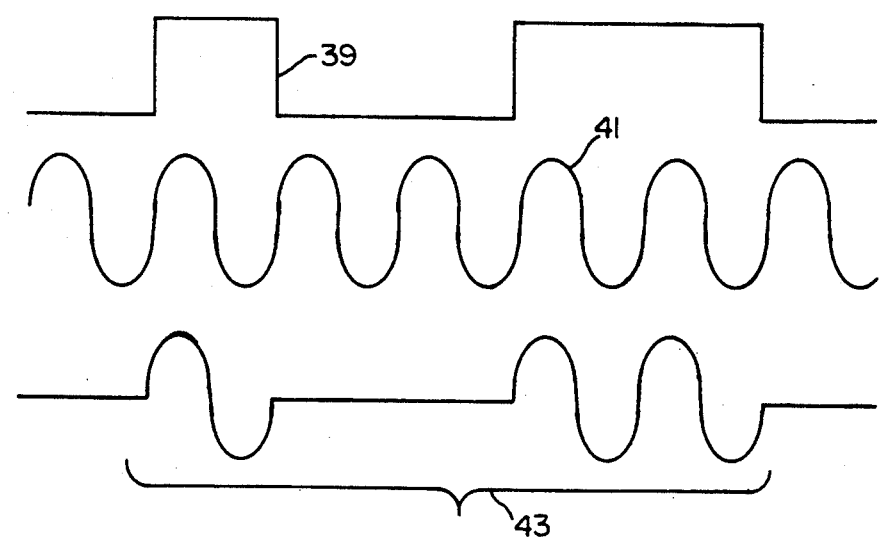
FIG. 3 is a simplified signal diagram showing the transmitted ultrasound signal.

While a variety of pseudo-random data signals can be used, an example is shown in FIG. 3, in which the data signal 39 is imposed on a carrier signal 41 to produce a signal burst 43, which in the embodiment shown has a duration of 7 microseconds. The pseudo-random signal may vary significantly with varying times between each such burst. One significant advantage of a pseudo-random transmit signal is that it permits the use of a low voltage (5 volt), low current signal to drive the individual transducer elements, and hence, low voltage digital output logic can be used to control and drive the transmitter. This not only significantly reduces cost and complexity of the required electronic drive circuitry for the transducer, it also permits the entire transmitter drive circuit to be implemented on a single monolithic chip. Further, low voltage is, of course, desirable from a safety standpoint, compared to the much higher voltages typically required by conventional ultrasound devices.

The transmitted signal is directed into the body of a user, to the bladder, and then rebounds from the bladder, forming an echo signal. This echo signal is picked up by a receiving antenna portion of transducer 30. The receiving antenna comprises a plurality of transducing elements separate from the plurality of transducer elements which define the transmitting antennas. Hence, there are separate transmit and receive antennas, i.e. at least one transmitting antenna (there are three in FIG. 4) and at least one receiving antenna defined within transducer 30 in the present embodiment. The arrangement of transducer 30 permits a close physical relationship between the transmitting and receiving antennas, respectively, but significantly reduces the noise impact on the receiver circuitry caused by transmitter circuitry, which would necessitate special protective elements, in the conventional approach, where the same transducer elements are used to both transmit and receive. Typically, the transmit pulse is much larger than the received pulse so that noise in the transmitted signal tends to drown out the received signal. This is overcome in the present invention. Another advantage to the described arrangement is that it does not restrict or limit the close-in range. While the transmit and receiving antennas are in fact physically separate, they are implemented as part of a single overall transducer so that simplicity is maintained.

In the present invention, there are two different receiver antenna arrangements defined within transducer 30 in FIG. 4. The first arrangement involves two sets of two spaced transducer arrays, with the two sets of arrays being positioned at 90° to each other. The two arrays in each set are spaced a given distance from each other. Transducer elements 2C through 2S and 19B through 19R (identified by the grid numerals/letters in FIG. 4) form one set, referred to in the drawings as bar receiver 00° (A,B), for 0°, while elements 2B-18B and 3S-19S form the other set, referred to as 90° (A,B), for 90°. Each pair of receiving arrays 00° (A,B) and 90° (A,B) operates similarly, but at 90° to each other.

The processing of the received signals proceeds as follows. Referring to FIG. 2, the rebounding echo signal is received first by the transducing elements in the first array 00° (A), assuming that the transmitted beam is in a 0° plane and angled toward the first 00° array, and thereafter by the second 00° array (B).

The signal received at the first plurality of 00° elements will be slightly ahead in time relative to the receipt of the signal at the second plurality of 00° elements. The receiving elements in the 00° arrays are readily aligned with the transmitter because of the configuration of the individual transducer elements of the transducer 30. With conventional receivers, the received signals are matched with time delay elements and then added to produce the composite received signal. In the embodiment shown, however, the received signals are applied, respectively, to preamplifiers 60, 62 and from there to time-controlled gain amplifiers 64 and 66. The amplified signals are then applied to analog-to-digital converters 70 and 72, which are controlled by a clock 74.

Figure 8:
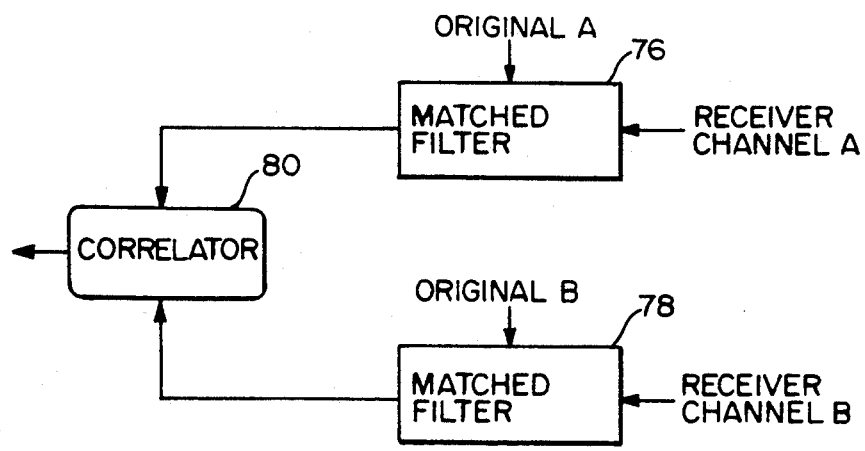
FIG. 8 is a block diagram of a portion of one receiver embodiment.

With conventional phase array processing using only two channels (as in the case effectively with the above-described arrangement), the result would have relatively poor directionality. However, the present invention overcomes that by use of a matched filter and correlator arrangement shown in FIG. 8. The digitized signals from the A/D converters 70, 72 are applied to matched filters 76 and 78. This occurs in the microprocessor 36 in FIG. 2. The matched filters multiply the received digitized signals by the original transmitted pseudo-random signal burst and then accumulate the result. This result corresponds to, i.e. shows, the degree of correlation in time between the transmitted signal burst and the received signal. When the transmitted signal burst and the received signal do substantially correlate, a very large, easily discernable signal result occurs, since the output of each matched filter is clearly the greatest when the original signal and the received signal are coincident, i.e. correlate. This locates the particular range with a resolution which is much more precise than the pulse length of the original transmission.

At this point, the matched filter clears the result and starts accumulating the next batch of received information. Each successive correlation event result provided by the filter represents an echo range-delay of one original pseudo-random signal burst. A correlator circuit 80 multiplies the matched results from the two filters. Since the timing of the original signal for one channel will be a timed-shifted duplicate of the original signal for the other channel, the correlator performs the actual beam forming function for the received signal. The correlator's largest output occurs when the time-shift delay between the two receiver signals matches the actual time of flight delay between the two arrays in each receiver set. Since the time of flight delay is related linearly to the angle of incidence of the received signal on the receiving antenna array elements, because the more oblique the angle, the longer the time delay, the angle of the received signal can be calculated. This is accomplished in microprocessor 36 using conventional formulas from ROM 38 and data from RAM 42. The results from the two channel processing embodiment described above are approximately equal to the results obtained when a large number of channels are added together.

The second receiver arrangement involves the use of a donut-shaped or, more specifically, an octagonal-shaped antenna arrangement comprising a particular plurality of transducing elements in transducer 30. In the present case, referring to FIG. 3, a first donut receiving antenna arrangement is referred to as receiver A and comprises elements H4, G5, E7, D8, D13, E14 G16, H17, M17, N16, p14, Q13, Q8, P7, N5 and M4. These 16 receiving elements are all connected by a cross-point multiplexer circuit in FPGA 40 (low resistance, low capacitance) onto one donut receiver channel A. Receiving elements D9, D10, D11, D12, I17, J17, K17, L17, Q12, Q11, Q10, Q9, L4, K4, J4, and I4 are multiplexed onto donut receiver channel B.

The received signals, multiplexed onto channels A and B, are digitized and beam-formed digitally in the traditional phased array manner involving the summation of the received signals. This process also occurs in the microprocessor 36. The digitized signals from each element are shifted in time by an amount which is proportional to the desired angle of incidence, and then summed into a final backscatter waveform. As discussed above, the 32 element signals are multiplexed onto two channels A and B. In operation, the original signal burst (pseudo-random) is transmitted and the received signal is stored in memory (RAM) for a first pair of receiver elements, after being digitized. The original signal is then re-transmitted in the same scan plane and with the same scan angle, but the received signals from a different pair of receiving elements are digitized and stored. This process is repeated 16 times to cover all 32 receiving elements.

Additional channels, i.e. four channels, would require a re-transmission of the original signal only eight times instead of 16 times. A large number of scan planes could also be used, with the process described above being repeated for each scan plane. In the embodiment shown, the scan planes are 0, 45, 90 and 135 degrees. With these particular scan planes, only eight passes (re-transmissions) are actually needed for all 32 receiving transducer elements, due to the octagonal arrangement of the receiving transducer elements and hence, identity of results for several elements.

An example of the above-described processing for a 0° scan plane is shown in FIG. 5. Each of the 32 elements in the receiver antenna array is connected to either channel A or channel B as described above and as shown in FIG. 5. The letter (A or B) at each transducer element position indicates the channel, and the number indicates the particular re-transmission (pass) of the transmitted signal burst when the received signal at that particular transducer element is processed and stored in memory. On the first pass, for instance, the received signals at the four transducer elements labeled B0 are applied in parallel to the channel B circuit while the received signals at the two A0 transducer elements are applied to the channel A circuit. On the second pass, the received signals at elements labeled A1 and B1 are processed and stored. This continues until the seventh pass has been completed. The stored signals are then timed-shifted in the manner also shown in FIG. 5. For instance, the signals A0 and B0 remain unshifted. Signal A1 in FIG. 5 is shifted by one unit of time delay (ud) and then added to the A0 and B0 signals. The signal A2 is shifted by three unit time delays and added to the previous result and so forth, with the signals A7 and B5 being shifted by 13 unit delays. The actual amount of the time delay represented by the "unit" delay depends on the scan angle of the transmitted beam. A direct or broadside (zero) scan angle will have zero unit delay, while the maximum scan angle (approximately 50° in the embodiment shown) will have the maximum unit delay. The 13 summed signals produce a composite received signal. Another example of the above-described receiving process is shown in FIG. 6, for a 45° scan plane. The composite received signal in this scan plane is produced as discussed above.

The resulting composite signal for each scan plane is stored in memory. Following a plurality of passes for several scan planes will typically produce sufficient information that the microprocessor can then determine by calculation the three-dimensional image of the actual bladder, in accordance with conventional ultrasound processing techniques using the actual dimensions of the bladder. Using the three-dimensional information, the volume of the bladder is then calculated using a conventional volume formula stored in ROM.

FIG. 9 is a simplified block diagram showing the steps in calculating the volume of the bladder from the beam-formed scan line data produced by the signal processing techniques described above. The step of beam-forming from the received data is shown at block 90 in FIG. 9. As shown in block 92, a median filter is then used on the data, the filter also converting the beam-formed data from spherical coordinates to rectangular coordinates, for simplification of follow-on processing. In the embodiment shown, there is a two-dimensional median filter for processing of each scan plane data, i.e. 0°, 45°, 90° and 135°. The median filter smoothens out the data and removes random spot noise. Processing data through a median filter includes the steps of processing small, successive "windows" of successive data points by summing the data in the window, dividing by the number of points in the window, and then moving the window along the string of input data by one location. The process of successive calculation is repeated until the entire string of input data is so processed, with the exception of the edge data, which is not processed.

Figure 11:
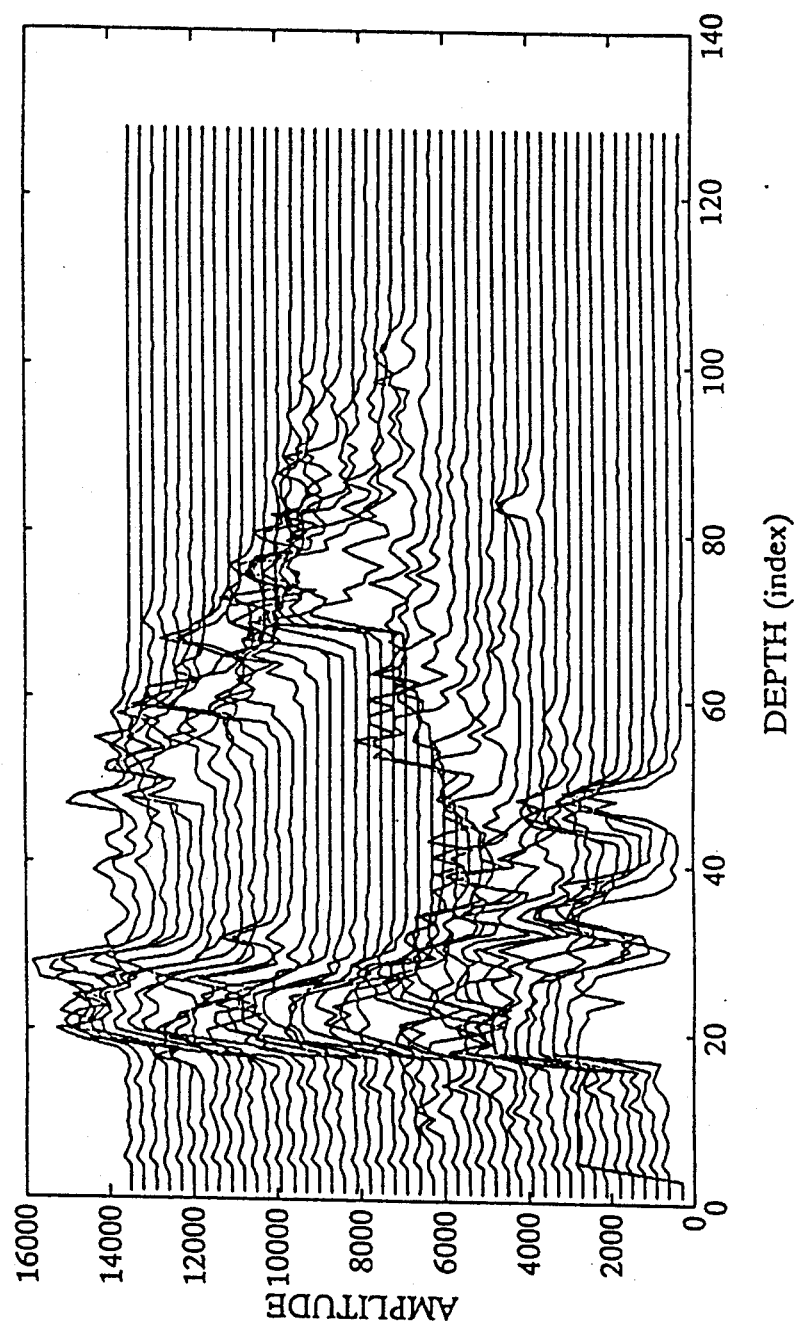
FIG. 11 is a composite signal diagram showing the outline of a scanned bladder for a single scan plane.

An example of the beam-formed data in FIG. 9 is shown in FIGS. 10A and 10B. FIG. 10A shows a single scan line data string which is at such an angle in a given scan plan such that it does not intersect the bladder, while FIG. 10B shows a scan line which does in fact intersect the bladder, showing the front wall at 94 and the back wall at 96. An entire scan plane of beam-formed data, comprising a plurality of scan line data, is shown in FIG. 11. This is referred to as a "waterfall" display and shows data for a particular scan plane which does in fact intersect the bladder.

In the next step of the process, shown at block 98, the data is processed to extract the boundary edge of the bladder for each scan line. A number of different techniques can be used to extract the edge information. In the embodiment shown, this is accomplished by a sobel filter, followed by a thresholding processing step. The sobel filter is a conventional technique for highlighting edges which appear as significant changes in amplitude in a given region. Examples of edge-extracted data for two complete scan planes (longitudinal axis and horizontal axis) are shown in FIGS. 12A and 12B.

The last step in the process involves the integration of the edge data to compute volume, as shown in block 101 in FIG. 9. The volume of randomly shaped bladders can be determined without a significant amount of computation, as can be seen from the above description. The leading edge of the individual scan planes in effect "slice through" the bladder at the various scan plane angles. Within the scan plane are a plurality of individual scan lines comprising the data along those lines within the scan plane. The calculation algorithm used in the present invention uses the scan line data in the several scan planes to construct outlines of successive cross-sections of the bladder from the front to the rear of the bladder, referred to as frontal planes. The area of each frontal plane is calculated from the outline information; an integration is performed in the Z (depth) dimension, i.e. from front to back. Each frontal plane area is multiplied by the depth to give an incremental volume. All the incremental volumes are then summed to provide a total volume.

The calculation of each frontal plane area depends on the number of scan planes used. If four scan planes are used, then the area is modeled on an ellipse, using the particular edge points identified. This is shown in FIG. 13A. With more scan planes, the outline can be determined with straight line approximations between adjacent scan lines. With fewer scan lines, i.e. two, the outline is assumed to be an ellipse. An advantage of four scan lines as opposed to two is that the bladder need not be centered in the imaging cone to obtain accurate information, as shown in FIG. 13B.

An alternative volume calculation involves what is referred to herein as a "voxel" method. The bladder is modeled as an arbitrary volume comprising a large plurality of small three-dimensional volumes. Each such volume is termed a voxel (volume pixel). Each scan line passes through a number of separate voxels. With sufficient spatial resolution, all the voxels within the boundary of the bladder can be determined and then summed to provide the bladder volume.

Figure 14:
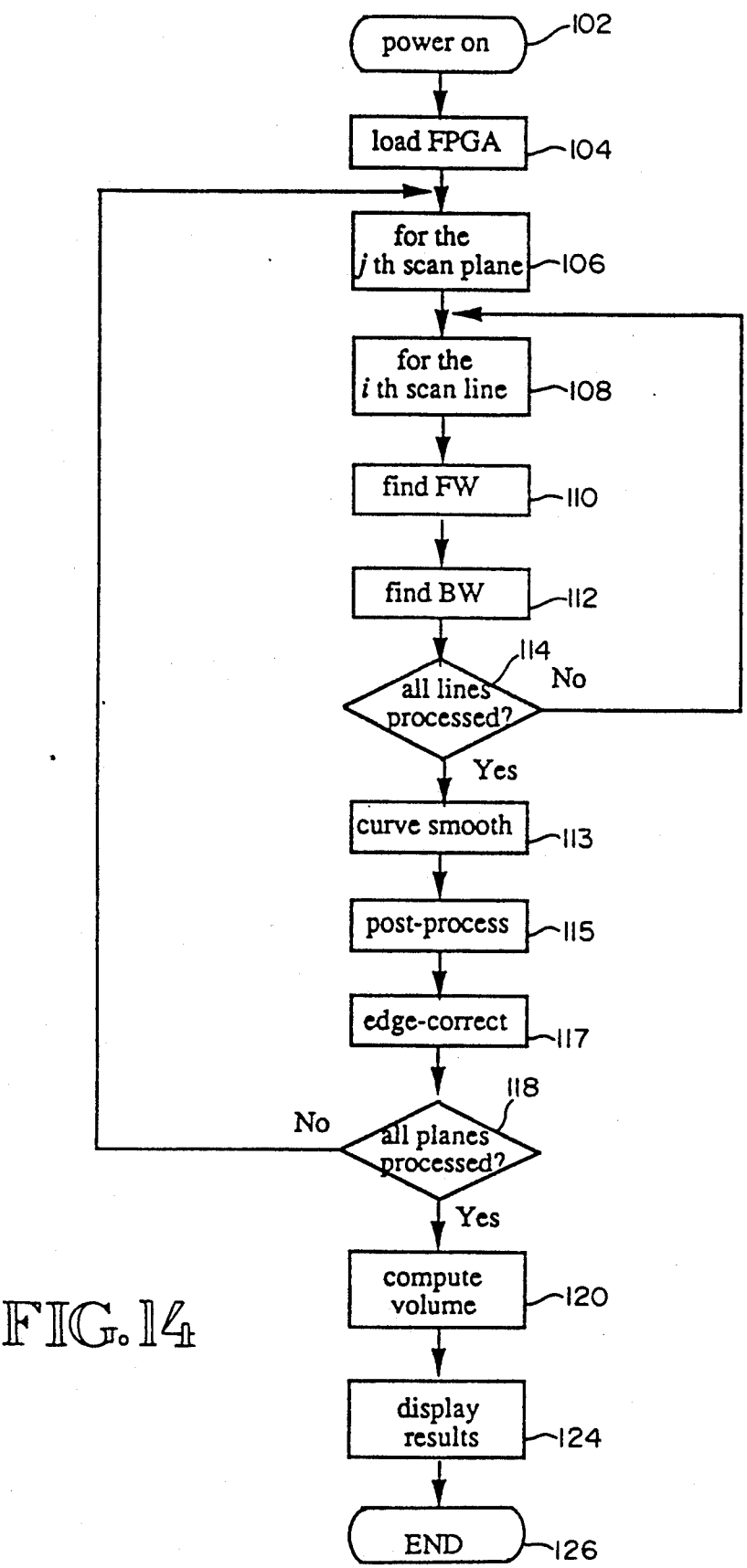
FIG. 14 is a block diagram of the flow of functional operations of the present invention.

FIG. 14 shows a basic functional flow chart for the operation of the apparatus of the present invention. The initial functional step for the apparatus, as indicated at block 102, is power-on. The field programmable gate array device (FPGA) is then loaded at block 104. As indicated above, the FPGA is a combination of RAM memory and various solid-state devices which accomplish particular functions, such as inverters, etc., controlled by the RAM and which interface the microprocessor and other elements in the apparatus.

The actual operation of the apparatus now begins. A first scan plane, i.e. the jth scan plane, as shown in block 106, is selected. The first scan line (ith scan line) within that first scan plane is then transmitted and received as shown in block 108. The received data is then processed to find first the front wall (block 110) and then the back wall of the bladder, as shown by block 112. This process continues, by means of a decision block 114, until all of the scan lines in a particular scan plane have been processed. When that is completed, the data is processed through a curve smoothing algorithm, shown in block 113, in which each wall "point" is compared with adjacent wall points. If a substantial difference is determined, a substitute wall point is produced which is the result of interpolation between the adjacent wall points. Then, referring to block 115, the total image is reviewed and only the largest bladder outline is maintained, in the event that more than one outline is produced. Lastly, the edge determination is subject to correction, as shown by block 117. In this step, the previous relatively tight criteria for FW/BW selections are lessened to improve the comprehensive image of the bladder, because of the now known general location of the bladder. As shown in decision box 118, the other scan planes are then processed, as set forth above for the jth scan plane, and the volume of the bladder is computed at block 120. The results are then displayed, at block 124. The operation of the apparatus is then terminated, as shown at 126.

Figure 1:
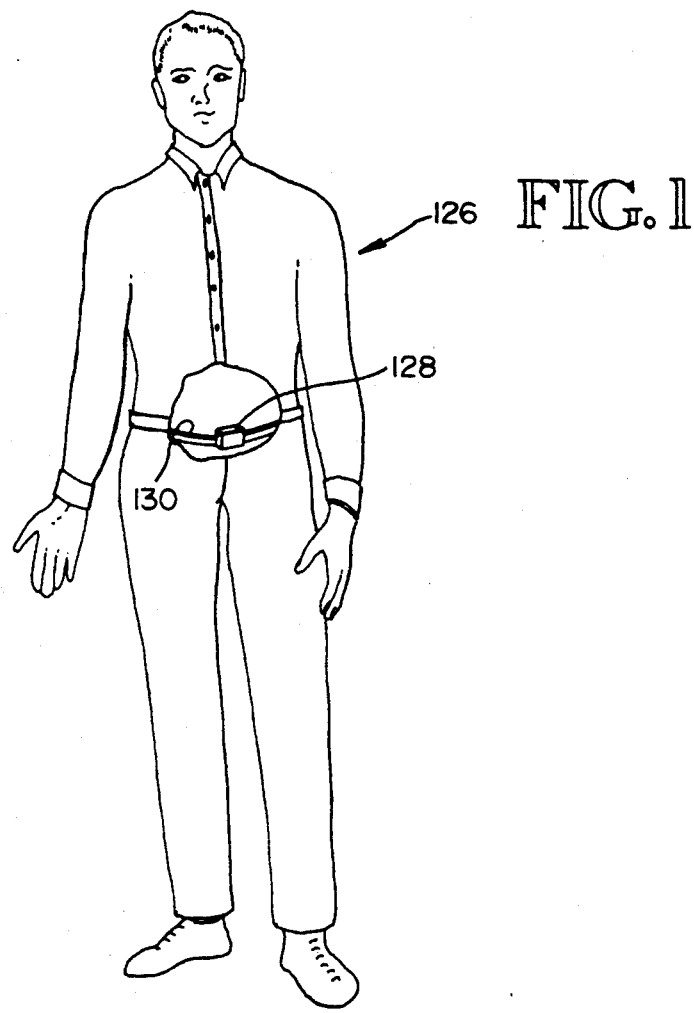
FIG. 1 is a view showing the apparatus of the present invention in position on a user.

The volume calculation may then be displayed on the face of the apparatus or by some other remote display apparatus. The apparatus is capable of operating on a continuous basis, i.e. transmitting and processing the received signals to produce successive volume calculations. FIG. 1 shows a patient 126 having the apparatus of the present invention 128 attached to him in the vicinity of the bladder, by a belt or similar article 130. Volume information can be stored in RAM memory in the apparatus over time and then transmitted to external memory and/or a printer (not shown) via an IR or radio link. Volume data can thus be developed conveniently over time. This information can be used by a physician (or the patient) in urological diagnosis, monitoring, and treatment. An alarm or other signal capability can also be provided on the patient when the volume of urine reaches a certain preselected level.

The present invention also includes other significant features. The first feature concerns a channel calibration system. Referring to FIG. 2, a broadside signal (the 0° scan line (angle) in the very axial center of the imaging cone) is transmitted with the receiver (FIG. 4) antenna having a "broadside" (BRD) configuration or arrangement, comprising the following elements: G4, F5, E6, D7, C8-13, D14, E15, F16, G17, H18, I18, J18, K18, L18, M18, N17, O16, P15, Z14, R13-8, Q7, p6, O5, N4, M3, L3, K3, J3, I3 and H3. The broadside transmitting transducer element configuration is connected to both receiver channels. The processed signals from the preamplifiers 60 and 62 on both channels are then compared to determine any differences which may exist. The difference is used to produce an offset calibration to produce equality in the processed signals between channels. This calibration is performed dynamically, in real time. This process can also be used to adjust for the operation of the time controlled amplifiers 64 and 66.

Figure 7A:
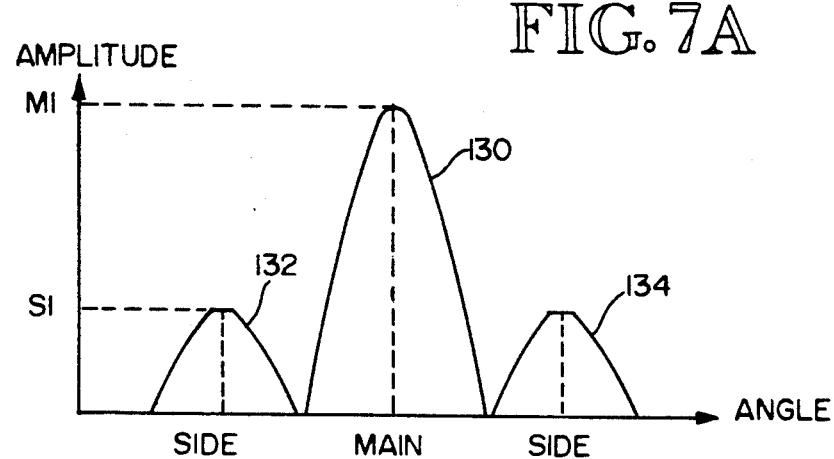
FIGS. 7A and 7B show 2 main beam/side lobe patterns for a received beam.
Figure 7B:
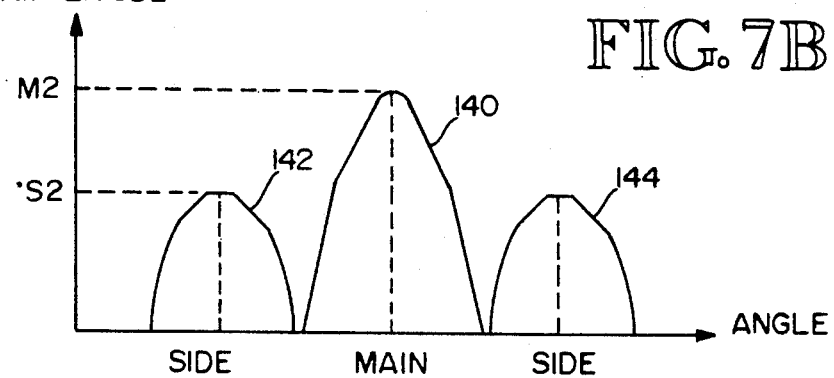

Second, the present invention includes a technique for improving the directivity of the receiving antenna. In the present arrangement, the antenna configurations discussed above with respect to FIG. 4 will produce different beam profiles in different passes. Side lobes and other undesired angular artifacts ideally exist at the same angle between the multiple passes, although the relative amplitudes of the side lobes and the main lobe will differ. The different side lobe and main lobe amplitudes are characterized such that the amplitude ratios could be determined and the signals could be accordingly processed to remove the side lobe contribution. As an example, referring to FIG. 7A, a first pass or transmission produces a main lobe 130 and side lobes of 132 and 134. A second pass might have a main lobe 140 at the same spatial angle as the main lobe 130 from the first pass but with a reduced amplitude. Similarly, the second pass side lobes 142, 144 have amplitudes which are greater than the side lobes 132, 134 of the first pass. The complete signal for each pass will comprise the response from the main lobe angle amplified by the main lobe amplitude and the response from each side lobe angle amplified by the side lobe response. If the measured response is u(t), where s(t) is the side lobe component and m(t) is the main lobe component, the response for the two passes can be expressed as follows:

$$u1(t) = S1 \cdot s(t) + M1 \cdot m(t)$$

$$u2(t) = S2 \cdot s(t) + M2 \cdot m(t)$$

Since S1, S2, M1, and M2 are known, and since the total responses are also known since they were directly measured, two equations result with two unknowns which can be expressed as follows:

$$m(t) = [S1u2(t) - S2u1(t)]/[S1M2 - S2M1]$$

The side lobe component has thus been eliminated relative to calculation of the main lobe component. This result is accomplished without any additional hardware. This side lobe processing technique can be used with any transmitter or receiver approach described herein.

Hence, a bladder imaging and volume calculation apparatus has been disclosed which involves particular ultrasound transmission and receiving techniques, including the use of a particular transducer assembly comprising a large number of individual transducing elements which are connected to form particular transmitting and receiving array configurations. Further, particular processing techniques are utilized in the receiver. All of this results in an instrument which is capable of automatically and completely imaging the bladder on a continuous basis and then calculating the volume thereof. The information may be stored on a continuous basis to provide a record of bladder volume over time which may then be printed out at selected intervals by means of a data transmission link. This accumulated data is particularly important since it can aid in the diagnosis and treatment of urological dysfunction. The device is conveniently wearable on the user, as shown in FIG. 1, and after some initial adjustment will provide the required information automatically without any operator intervention. The device thus can be used on an out-patient basis, in a normal living routine.

In addition, while the present invention is useful primarily to image the bladder and calculating volume based on that image, it can also be used conveniently and without substantial modification to image other organs in the body, such as portions of the heart or the prostate. Hence, the present invention is not limited to bladder volume applications.

Although a preferred embodiment of the invention has been disclosed herein for illustration, it should be understood that various changes, modifications and substitutions may be incorporated in the embodiment without departing from the spirit of the invention which is defined by the claims which follow:

What is claimed is:

1. An apparatus for automatically scanning a bodily organ, and producing organ image information, comprising:
   a transmitter comprising a plurality of transmitter transducer elements arranged in a preselected pattern, producing a transmitting signal beam which can be directed toward the organ;
   means for energizing the transmitter transducer elements so as to produce a transmitted signal comprising a series of complex signal bursts, wherein the complex signal is a pseudo-random signal; and
   means for receiving an echo signal from the organ and producing information representative of the image of at least a portion of the organ in three dimensions.

2. An apparatus of claim 1, wherein the organ is a bladder and the apparatus includes means for calculating the volume of said bladder and hence the volume of urine in the bladder, from said representative information.

3. An apparatus of claim 2, wherein the preselected pattern of transmitter transducer elements is open in the center thereof.

4. An apparatus of claim 3, wherein the preselected pattern is approximately circular.

5. An apparatus of claim 2, wherein the receiving means comprises a preselected arrangement of transducer elements and wherein the receiving means and the transmitter are positioned so as to form a single transducer assembly.

6. An apparatus of claim 5, wherein the transducer assembly comprises an array of closely spaced transducer elements, a first plurality of said transducer elements being energized to produce a transmitting beam, and a second plurality of elements being arranged and connected to receive the echo signal, wherein the transducer elements are closely spaced, but the fist plurality of transducer elements being physically separate from the second plurality of transducer elements.

7. An apparatus of claim 6, wherein the first plurality of transducer elements comprises three separate sub-pluralities of transducer elements, said sub-pluralities forming concentric, approximately circular, transmitting antennas to provide differing depths of signal penetration.

8. An apparatus of claim 7, wherein the three transmitting antennas are, respectively, 8, 10, and 12 wavelengths in diameter.

9. An apparatus of claim 6, wherein the second plurality of transducer elements includes first and second sets of spaced linear arrays of transducer elements, each set being at approximately 90 degrees to each other and a third set of transducer elements arranged into an approximately circular configuration, wherein the third set of transducer elements is located within an area bounded by said first and second sets of transducer elements.

10. An apparatus of claim 2, wherein the receiving means includes at least two sets of arrays of receiving transducer elements, the arrays comprising each set being spaced apart from each other, and further includes means for correlating the echo signals received by each array with the transmitted signal and for multiplying the received signals to form a composite signal when a maximum correlation is obtained for each array.

11. An apparatus of claim 10, wherein each set of arrays includes two linear arrangements of receiving transducer elements and wherein the two sets of arrays are positioned 90° relative to each other.

12. An apparatus of claim 10, wherein the transmitter and receiving transducer elements form a transducer assembly and wherein the receiving transducer elements are positioned in the vicinity of the periphery of the transducer assembly.

13. An apparatus of claim 10, wherein the received signals in each array are applied to two separate channels and wherein the apparatus includes means for calibrating the two channels by applying a calibrating signal directly to said two channels, determining the difference in any results, and compensating for the difference, so that the effect of the two channels on received signals will be approximately the same.

14. An apparatus of claim 2, wherein the receiving means includes a plurality of receiving transducer elements, arranged in a selected pattern, means for obtaining received signals from successive, different pluralities of receiving elements in response to successive transmitted signals, means for directing at least one of the received signals from each successive plurality of receiving elements to a first channel and for directing at least another one of the received signals from each successive plurality of receiving elements to a second channel, means for amplifying the signals in each channel and means for time-shifting the results and then adding the time-shifted signals to form a composite received signal, wherein said composite received signal can be used to produce the information which is representative of the image of the bladder.

15. An apparatus of claim 14, wherein the selected pattern of receiving transducer elements is approximately octagonal, and wherein the successive transmitted signals include at least four transmitted signals, spaced at selected angles relative to each other in successive scan planes.

16. An apparatus of claim 15, wherein the successive scan planes occur at 0, 45, 90 and 135 degrees.

17. An apparatus of claim 14, including means for calibrating the two channels by applying a calibrating signal directly to said two channels, determining the difference in any results and then compensating for the difference so that the effect of the two channels on received signals will be approximately the same.

18. An apparatus of claim 2, including means for maintaining a record of bladder volume over time.

19. An apparatus of claim 10, including means for providing said bladder volume information to an external printer.

20. An apparatus of claim 2, wherein the apparatus is arranged so as to be worn by the user.

21. An apparatus of claim 2, wherein the volume calculating means includes means for calculating the volume of successive planar portions of the bladder from the three-dimensional image information from a front surface of the bladder to a rear surface thereof, the planar portions having a depth which is sufficiently small that the calculation approaches an integration 22. An apparatus of claim 1, wherein the transmitter transducer elements are energized by a low voltage signal, and wherein the energizing means includes a transmitter drive circuit which is low voltage and can be implemented on a single chip.

23. An apparatus of claim 1, including means for processing received echo signals to substantially eliminate the side lobe contribution.

24. An apparatus of claim 23, wherein the side lobe processing means includes means for calculating the main lobe component using the received signal and the known side lobes of successive scans.

25. An apparatus of claim 1, wherein the organ is a heart.

26. An apparatus for automatically scanning a bladder to develop a three-dimensional image thereof, comprising:
   a transmitter for producing a transmitting beam which is directed toward the bladder;
   means for automatically controlling the transmitter so as to produce a plurality of spaced scan line signals within a first scan plane at a selected angle and within successive scan planes at successive selected angles; and
   means for receiving an echo signal from the bladder and producing information representative of the image of the bladder in three dimensions, wherein the receiving means includes at least two sets of arrays of receiving transducer elements, the arrays comprising each set being spaced apart from each other, and further includes means for correlating the echo signals received by each array with the transmitted signal and for multiplying the received signals to form a composite signal when a maximum correlation is obtained for each array.

27. An apparatus of claim 26, wherein the first scan plane and the successive scan planes comprise at least four scan planes.

28. An apparatus of claim 26, wherein the transmitter comprises a plurality of transmitter transducing elements arranged in a preselected pattern to produce the transmitting beam.

29. An apparatus of claim 28, wherein the preselected pattern of transmitter transducing elements is open in the center thereof.

30. An apparatus of claim 28, wherein the receiving means comprises a preselected arrangement of transducer elements and wherein the receiving means and the transmitter are positioned so as to form a single transducer assembly.

31. An apparatus of claim 28, wherein the plurality of transmitting transducer elements comprises three separate sub-pluralities of transducer elements, said sub-pluralities forming concentric, approximately circular transmitting antennas to provide differing depths of signal penetration.

32. An apparatus of claim 26, wherein each set of arrays includes two linear arrangements of receiving transducer elements and wherein the two sets of arrays are positioned 90° relative to each other.

33. An apparatus of claim 26, including means for processing received echo signals to substantially eliminate the side lobe contribution.

34. An apparatus of claim 33, wherein the side lobe processing means includes means for calculating the main lobe component using the received signal and the known side lobes of successive scans.

35. An apparatus of claim 26, including means for maintaining a record of bladder volume over time.

36. An apparatus of claim 26, wherein the apparatus is arranged so as to be worn by the user.

37. An apparatus of claim 26, including means for calculating the volume of the bladder by calculating the volume of successive planar portions of the bladder from the three-dimensional image information from a front surface of the bladder to a rear surface thereof, the planar portions having a depth which is sufficiently small that the calculation approaches an integration function.

38. An apparatus for automatically scanning a bladder and to produce volume information, comprising:
 a transmitter for producing a transmitting beam which is directed toward the bladder;
 means for receiving an echo signal from the bladder and producing information representative of the image of the bladder in three dimensions;
 means for calculating the volume of the bladder and hence the amount of urine in the bladder, from said representative information; and
 means for storing the volume information over time, so as to provide a history of bladder volume information for a patient, wherein the apparatus is adapted so as to be carried on a patient during daily activity for periodic scanning of the bladder and calculation and storage of volume information developed therefrom.

39. An apparatus of claim 38, wherein the transmitter comprises a plurality of transmitter transducing elements arranged in a preselected pattern to produce the transmitting beam.

40. An apparatus of claim 39, wherein the preselected pattern of transmitter transducing elements is open in the center thereof.

41. An apparatus of claim 39, wherein the receiving means comprises a preselected arrangement of receiver transducer elements and wherein the receiver transducer elements and the transmitter transducer elements are positioned so as to form a single transducer assembly.

42. An apparatus of claim 39, wherein the receiving means includes at least two sets of arrays of receiving transducer elements, the arrays comprising each set being spaced apart from each other, and further includes means for correlating the echo signals received by each array with the transmitted signal and for multiplying the received signals to form a composite signal when a maximum correlation is obtained for each array.

43. An apparatus of claim 42, wherein each set of arrays includes two linear arrangements of receiving transducer elements and wherein the two sets of arrays are positioned 90° relative to each other.

44. An apparatus of claim 38, wherein the receiving means includes a plurality of receiving transducer elements, arranged in a selected pattern, means for obtaining received signals from successive, different pluralities of receiving elements in response to successive transmitted signals, means for directing at least one of the received signals from each successive plurality of receiving elements to a first channel and for directing at least another one of the received signals from each successive receiving elements to a second channel, means for amplifying the signals in each channel and means for time-shifting the results and then adding the time-shifted signals to form a composite received signal, wherein said composite received signal can be used to produce the information which is representative of the image of the bladder.

45. An apparatus of claim 38, including means for providing said bladder volume information to an external printer.

46. An apparatus of claim 38, wherein the volume calculating means includes means for calculating the volume of successive planar portions of the bladder from the three-dimensional image information from a front surface of the bladder to a rear surface thereof, the planar portions having a depth which is sufficiently small that the calculation approaches an integration function.

47. An apparatus for automatically scanning a bodily organ, and producing organ image information, comprising:
 a transmitter comprising a plurality of discreet transmitter transducing elements arranged and connected in a pattern which defines an open center area substantially surrounded by said transducing elements, in which said center area there are no transmitter transducing elements, the transmitter producing a transmitting signal beam which can be directed toward the organ;
 means for receiving an echo signal from the organ; and
 means responsive to said echo signal to produce information representative of the image of at least a portion of the organ.

48. An apparatus of claim 47, wherein the representative information is three-dimensional information.

49. An apparatus of claim 47, wherein the pattern of transmitter transducing elements is approximately circular.

50. An apparatus of claim 47, wherein the receiving means comprises a preselected arrangement of receiver transducer elements and wherein the receiver transducer elements and the transmitter transducer elements are positioned so as to form a single transducer assembly.

51. An apparatus of claim 47, wherein the organ is a bladder.

52. An apparatus of claim 47, wherein the receiving means includes at least two sets of arrays of receiving transducer elements, the arrays comprising each set of arrays being spaced apart from each other, the receiving means further including means for correlating the echo signals received by each array with the transmitted signal and for multiplying the received signals to form a composite signal when a maximum correlation is obtained for each array.

53. An apparatus of claim 52, wherein each set of arrays includes two linear arrangements of receiving transducer elements and wherein the two sets of arrays are positioned 90° relative to each other.

54. An apparatus of claim 47, wherein the receiving means includes a plurality of receiving transducer elements, arranged in a selected pattern, means for obtaining received signals from successive, different pluralities of receiving elements in response to successive transmitted signals, means for directing at least one of the received signals from each successive plurality of receiving elements to a first channel and for directing at least another one of the received signals from each successive plurality of receiving elements to a second channel, means for amplifying the signals in each channel and means for time-shifting the results and then adding the time-shifted signals to form a composite received signal, wherein said composite received signal can be used to produce the information which is representative of the image of the organ.

55. An apparatus of claim 54, wherein the selected pattern of receiving transducer elements is approximately octagonal, and wherein the successive transmitted signals include at least four transmitted signals, spaced at selected angles relative to each other in successive scan planes.

56. An apparatus of claim 55, wherein the successive scan planes occur at 0, 45, 90 and 135 degrees.

57. An apparatus of claim 47, wherein the transmitting transducer elements comprise three separate subpluralities of transducer elements, said subpluralities forming concentric, approximately circular transmitting antennas to provide differing depths of signal penetration.

58. An apparatus for automatically scanning a bladder to develop a three-dimensional image thereof, comprising:
a transmitter for producing a transmitting beam which is directed toward the bladder;
means for automatically controlling the transmitter so as to produce a plurality of spaced scan line signals within a first scan plane at a selected angle and within successive scan planes at successive selected angles; and
means for receiving an echo signal from the bladder and producing information representative of the image of the bladder in three dimensions, wherein the receiving means includes a plurality of receiving transducer elements, arranged in a selected pattern, means for obtaining received signals from successive different pluralities of receiving elements in response to successive transmitted signals, means for directing at least one of the received signals from each successive plurality of receiving elements to a first channel and for directing at least another one of the received signals from each successive plurality of receiving elements to a second channel, means for amplifying the signals in each channel and means for time-shifting the results and then adding the time-shifted signals to form a composite received signal, wherein said composite received signal can be used to produce the information which is representative of the image of the bladder.

59. An apparatus of claim 58, wherein the first scan plane and the successive scan planes comprise at least four scan planes.

60. An apparatus of claim 58, wherein the transmitter comprises a plurality of transmitter transducing elements arranged in a preselected pattern to produce the transmitting beam.

61. An apparatus of claim 60, wherein the preselected pattern of transmitter transducing elements is open in the center thereof.

62. An apparatus of claim 60, wherein the receiving means comprises a preselected arrangement of transducer elements and wherein the receiving means and the transmitter are positioned so as to form a single transducer assembly.

63. An apparatus of claim 60, wherein the plurality of transmitting transducing elements comprises three separate sub-pluralities of transducer elements, said sub-pluralities forming concentric, approximately circular transmitting antennas to provide differing depths of signal penetration.

64. An apparatus or claim 58, including means for processing received echo signals to substantially eliminate the side lobe contribution.

65. An apparatus of claim 64, wherein the side lobe processing means includes means for calculating the main lobe component using the received signal and the known side lobes of successive scans.

66. An apparatus of claim 58, including means for maintaining a record of bladder volume over time.

67. An apparatus of claim 58, wherein the apparatus is arranged so as to be worn by the user.

68. An apparatus of claim 58, including means for calculating the volume of the bladder by calculating the volume of successive planar portion so the bladder from the three-dimensional image information from a front surface of the bladder to a rear surface thereof, the planar portions having a depth sufficiently small that the calculation approaches an integration function.

69. An apparatus for automatically scanning a bladder to develop a three-dimensional image thereof, comprising:
a transmitter for producing a transmitting beam which is directed toward the bladder, wherein the transmitter comprises a plurality of transmitter transducing elements arranged in a preselected pattern to produce the transmitting beam, the plurality of transmitting transducer elements comprising three separate sub-pluralities of transducer elements, said sub-pluralities forming concentric, approximately circular transmitting antennas to provide differing depths of signal penetration;

means for automatically controlling heat transmitter so as to produce a plurality of spaced scan line signals within a first scan plane at a selected angle and within successive scan planes at successive selected angles; and means for receiving an echo signal from the bladder and producing information representative of the image of the bladder in three dimensions.

70. An apparatus of claim 69, wherein the first scan plane and the successive scan planes comprise at least four scan planes.

71. An apparatus of claim 69, wherein the receiving means comprises a preselected arrangement of transducer elements and wherein the receiving means and the transmitter are positioned so as to form a single transducer assembly.

* * * * *

UNITED STATES PATENT AND TRADEMARK OFFICE
CERTIFICATE OF CORRECTION

PATENT NO. : 5,235,985
DATED : August 17, 1993
INVENTOR(S) : McMorrow et al.

It is certified that error appears in the above-indentified patent and that said Letters Patent is hereby corrected as shown below:

Column 11, claim 6, line 7, the word "fist" should be --first--.

Column 12, claim 19, should be dependent on claim --18--.

Column 12, claim 21, line 7, the word --function-- should be inserted after the word "integration".

Column 16, claim 68, line 3, the word "so" should be --of--.

Column 16, claim 68, line 51, "portion" should read --portions--.

Signed and Sealed this

Twenty-ninth Day of March, 1994

Attest:

BRUCE LEHMAN

Attesting Officer

Commissioner of Patents and Trademarks